United States Patent [19]

Nakao et al.

[11] 4,258,185

[45] Mar. 24, 1981

[54] PYRIDAZINONE COMPOUNDS

[75] Inventors: Toru Nakao, Nakatsu; Shinro Setoguchi; Osamu Yaoka, both of Fukuoka, all of Japan

[73] Assignee: Yoshitomi Pharmaceutical Industries, Ltd., Osaka, Japan

[21] Appl. No.: 139,625

[22] Filed: Apr. 14, 1980

Related U.S. Application Data

[63] Continuation-in-part of Ser. No. 952,183, Oct. 17, 1978, abandoned.

[51] Int. Cl.³ .................. C07D 401/04; A61K 31/50
[52] U.S. Cl. .................. 544/114; 544/238; 546/157; 546/158; 260/325 R; 424/250
[58] Field of Search .................. 544/114, 238

[56] References Cited

U.S. PATENT DOCUMENTS

| | | | |
|---|---|---|---|
| 3,316,267 | 4/1967 | Shen | 544/238 |
| 3,689,652 | 9/1972 | Curran et al. | 424/250 |
| 3,746,712 | 7/1973 | Ross | 424/250 |
| 3,812,256 | 5/1974 | Curran et al. | 424/250 |
| 3,822,260 | 7/1974 | Curran et al. | 260/465 D |
| 3,876,786 | 4/1975 | McEvoy et al. | 424/250 |
| 3,876,787 | 4/1975 | McEvoy et al. | 424/250 |
| 3,929,812 | 12/1975 | Denzel et al. | 544/238 |
| 3,931,177 | 1/1976 | Coates et al. | 424/248 |
| 3,944,551 | 3/1976 | Regnier et al. | 544/238 |
| 4,026,891 | 5/1977 | Austel et al. | 544/238 |

FOREIGN PATENT DOCUMENTS 2151216 4/1973 Fed. Rep. of Germany.
1157045 7/1969 United Kingdom .................. 544/114

*Primary Examiner*—Donald G. Daus
*Assistant Examiner*—James H. Turnipseed
*Attorney, Agent, or Firm*—Sughrue, Rothwell, Mion, Zinn and Macpeak

[57] ABSTRACT

Pyridazinone compounds of the formula:

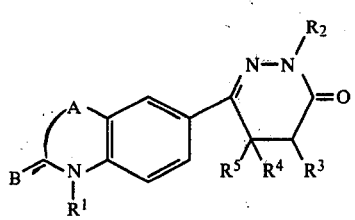

wherein A, B, $R^1$, $R^2$, $R^3$, $R^4$ and $R^5$ are as defined hereinafter, and pharmaceutically acceptable acid addition salts thereof are disclosed. They are useful as antithrombotic and antihypertensive drugs.

15 Claims, No Drawings

PYRIDAZINONE COMPOUNDS

This application is a continuation-in-part of copending application Ser. No. 952,183, filed Oct. 17, 1978, now abandoned.

This invention relates to pyridazinone compounds which are therapeutically useful as antithrombotic and antihypertensive drugs.

According to the present invention, there is provided a pyridazinone compound of the formula:

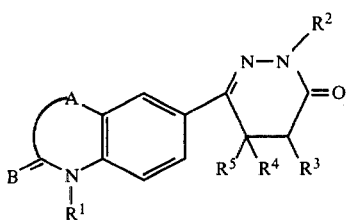

and a pharmaceutically acceptable acid addition salt thereof, wherein A is a methylene group, an ethylene group or a vinylene group in the case where A is an ethylene group or a vinylene group, it may be substituted by a lower alkyl group (e.g. methyl, ethyl, propyl or butyl); $B=C<$ is $O=C<$ or $H_2C<$; $R^1$ is a hydrogen atom, a lower alkyl group (e.g. methyl, ethyl, propyl or butyl), an alkanoyl group (e.g. acetyl, propionyl or butyryl), an alkylsulfonyl group (e.g. methanesulfonyl or ethanesulfonyl) or a benzoyl group which may be substituted by at least one substituent at any position(s) on the phenyl nucleus, each substituent being independently selected from a halogen atom (e.g. fluorine, chlorine or bromine), a lower alkyl group (e.g. methyl, ethyl, propyl or butyl) or a lower alkoxy group (e.g. methoxy or ethoxy); $R^2$ is a hydrogen atom, an alkyl group (e.g. methyl, ethyl, propyl, butyl, pentyl, hexyl, heptyl, octyl, nonyl, decyl, pentadecyl, hexadecyl, heptadecyl, octadecyl, nonadecyl, eicosyl, heneicosyl or docosyl), a hydroxy lower alkyl group (e.g. hydroxymethyl, 2-hydroxyethyl or 3-hydroxypropyl), a carbamoylalkyl group (e.g. carbamoylhexyl, carbamoyloctyl, carbamoyldecyl or carbamoylundecyl), a naphthyloxyalkyl group (e.g. naphthyloxymethyl or 2-naphthyloxyethyl), an oxoalkyl group (e.g. 3-oxobutyl or 4-oxopentyl) or a $(R^6)(R^7)N-(CH_2)_n-$ group, where each of $R^6$ and $R^7$ is a hydrogen atom or a lower alkyl group (e.g. methyl, ethyl, propyl or butyl) or $R^6$ and $R^7$ together with the adjacent nitrogen atom form a heterocycle (e.g. pyrrolidine, piperidine, morpholine, piperazine or N-methylpiperazine) and n is 2 or 3; $R^3$ is a hydrogen atom; $R^4$ is a hydrogen atom, a lower alkyl group (e.g. methyl, ethyl, propyl or butyl), a hydroxymethyl group or a lower alkanoyloxymethyl group (e.g. acetoxymethyl, propionyloxymethyl or butyryloxymethyl); and $R^5$ is a hydrogen atom or a lower alkyl group (e.g. methyl, ethyl, propyl or butyl); or $R^3$ and one of $R^4$ and $R^5$ together form a single bond.

Preferable compounds of the formula (I) are those wherein A is an ethylene group or a vinylene group which may be substituted by a lower alkyl group; $B=C<$ is $O=C<$; $R^1$ is a hydrogen atom or a lower alkyl group; $R^2$ is a hydrogen atom, an alkyl group or a $(R^6)(R^7)N-(CH_2)_n-$ group, where each of $R^6$ and $R^7$ is a hydrogen atom or a lower alkyl group or $R^6$ and $R^7$ together with the adjacent nitrogen atom form a heterocycle and n is 2 or 3; $R^3$ is a hydrogen atom; $R^4$ is a hydrogen atom, a lower alkyl group, a hydroxymethyl group or a lower alkanoyloxymethyl group; and $R^5$ is a hydrogen atom or a lower alkyl group.

More preferable compounds of the formula (I) are those wherein A is an ethylene group which may be substituted by a lower alkyl group; $B=C<$ is $O=C<$; $R^1$ is a hydrogen atom or a lower alkyl group; $R^2$ is a hydrogen atom, a lower alkyl group or a $(R^6)(R^7)N-(CH_2)_n-$ group, where each of $R^6$ and $R^7$ is a hydrogen atom or a lower alkyl group or $R^6$ and $R^7$ together with the adjacent nitrogen atom form a heterocycle and n is 2 or 3; $R^3$ is a hydrogen atom; $R^4$ is a hydrogen atom, a lower alkyl group, a hydroxymethyl group or a lower alkanoyloxymethyl group; and $R^5$ is a hydrogen atom.

The compound of formula (I) can be prepared by reacting a compound of the formula:

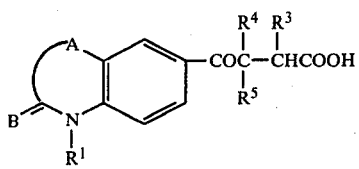

wherein each symbol is as defined above, or a functional derivative (e.g. an ester or an acid anhydride) thereof or a compound of the formula:

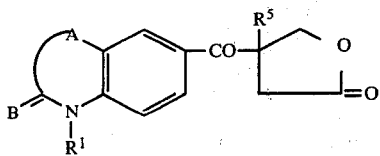

wherein each symbol is as defined above, with a compound of the formula:

$$R^2NHNH_2 \quad\quad (IV)$$

wherein $R^2$ is as defined above, or hydrate thereof, thereafter the product obtained, if desired, is esterified, alkylated, acylated, sulfonated, dyhydrogenated or converted into a pharmaceutically acceptable acid addition salt.

The reaction of the compound of formula (II) with the compound of formula (IV) is usually carried out without a solvent or in an inert solvent such as water, methanol, ethanol, propanol, isopropanol, tetrahydrofuran, dioxane, benzene, toluene, chloroform, dimethylformamide or a mixture thereof at room temperature or under heating.

The reaction of the compound of formula (III) with the compound of formula (IV) is preferably carried out by heating under reflux for 1 to 20 hours in a solvent such as methanol, ethanol or isopropanol.

The compound of formula (I) wherein $R^4$ is a lower alkanoyloxymethyl group can be prepared by esterifying the compound of formula (I) wherein $R^4$ is a hydroxymethyl group. The reaction is advantageously carried out by heating under reflux for 1 to 10 hours in the presence of a base such as triethylamine or pyridine in an inert solvent such as chloroform, dimethylformamide or tetrahydrofuran. The esterifying agent, for example, includes acetic acid, propionic acid, butyric acid or a functional derivative (e.g. an acid anhydride or an acid halide) thereof.

The compound of formula (I) wherein $R^2$ is other than a hydrogen atom can be prepared by alkylating the compound of formula (I) wherein $R^2$ is a hydrogen atom. The reaction is preferably carried out at a temperature of from 0° to 100° C. for 1 to 10 hours in the presence of a suitable deacidifying agent such as sodium hydride, sodium methoxide or sodium amide in a solvent such as dimethylformamide, dimethylsulfoxide, dimethylacetamide, N-methylpyrrolidone or tetrahydrofuran. The alkylating agent includes an alkyl halide (e.g. methyl iodide, ethyl bromide, butyl bromide, octyl bromide or docosyl bromide), a hydroxy lower alkyl halide (e.g. 2-hydroxyethyl bromide or 3-hydroxypropyl bromide), a carbamoylalkyl halide (e.g. 10-carbamoyldecyl bromide), a naphthyloxyalkyl halide (e.g. 2-(2-naphthyloxy)ethyl bromide), an oxoalkyl halide (e.g. 4-oxopentyl bromide), $(R^6)(R^7)N—(CH_2)_n—Hal$, wherein $R^6$, $R^7$ and n are as defined above and Hal is a halogen atom, such as 2-dimethylaminoethyl bromide, 3-dimethylaminopropyl bromide, 2-morpholinoethyl bromide or 3-piperidinopropyl bromide), or a corresponding organic sulfonate (e.g. methyl methanesulfonate or methyl p-toluenesulfonate) or sulfate (e.g. dimethyl sulfate).

The compound of formula (I) wherein $B=C<$ is $H_2C<$ and $R^1$ is an alkanoyl group, an alkylsulfonyl group or a benzoyl group which may be substituted by at least one substituent at any position(s) on the phenyl nucleus, each substituent being independently selected from a halogen atom, a lower alkyl group or a lower alkoxy group can be prepared by reacting a compound of the formula (I) wherein $B=C<$ is $H_2C<$ and $R^1$ is a hydrogen atom with an acylating agent such as an acid anhydride or an acid halide or an alkylsulfonyl halide such as methanesulfonyl chloride. The reaction is advantageously carried out in a suitable solvent such as benzene, toluene, chloroform or dioxane, if desired, in the presence of a deacidifying agent such as sodium carbonate, potassium carbonate, pyridine which can also be used as a solvent or triethylamine.

The compound of formula (I) wherein $B=C<$ is $H_2C<$ and $R^1$ is a hydrogen atom can be prepared by hydrolyzing a compound of the formula (I) wherein $B=C<$ is $H_2C<$ and $R^1$ is an alkanoyl group, an alkylsulfonyl group or a benzoyl group which may be substituted by at least one substituent at any position(s) on the phenyl nucleus, each substituent being independently selected from a halogen atom, a lower alkyl group or a lower alkoxy group. The hydrolysis is preferably carried out by heating under reflux in the presence of sodium hydroxide in an alcohol.

The compound of formula (I) wherein $R^3$ and one of $R^4$ and $R^5$ together form a single bond can be prepared by dehydrogenating a compound of the formula (I) wherein $R^3$ is a hydrogen atom, $R^4$ is a hydrogen atom, a lower alkyl group, a hydroxymethyl group or a lower alkanoyloxymethyl group and $R^5$ is a hydrogen atom and a lower alkyl group. The reaction is preferably carried out at a temperature of from 0° to 100° C. for several hours to scores of hours in the presence of a dehydrogenating agent such as bromine or chlorine with or without an inert solvent such as chloroform, dichloroethane, benzene, toluene or acetic acid.

The compound of formula (I) wherein A is a vinylene group which may be substituted by a lower alkyl group can be prepared by dehydrogenating a compound of the formula (I) wherein A is an ethylene group which may be substituted by a lower alkyl group. The reaction is preferably carried out at room temperature or under reflux for several hours to scores of hours in the presence of a dehydrogenating agent such as 2,3-dichloro-5,6-dicyano-1,4-benzoquinone, 2,3,5,6-tetrachloro-1,4-benzoquinone or palladium-carbon in an inert solvent such as methanol, benzene, toluene, xylene or dioxane.

The compounds of the present invention can be converted in a conventional manner into the corresponding acid addition salts with various inorganic or organic acids such as hydrochloric, hydrobromic, sulfuric, maleic, fumaric, oxalic and citric acids.

The starting compounds of formulas (II) and (III) can be prepared by such a conventional manner as described in the following reaction scheme:

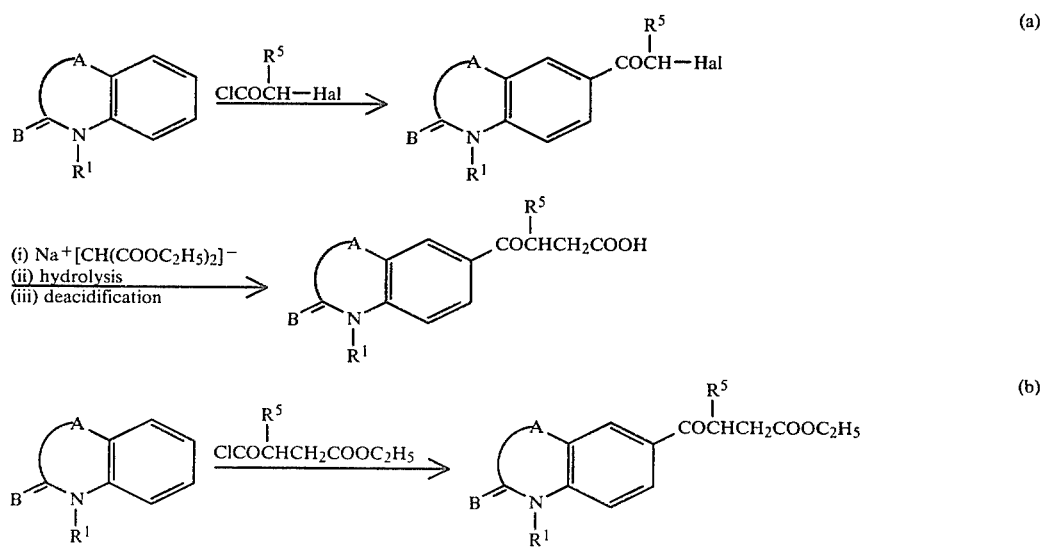

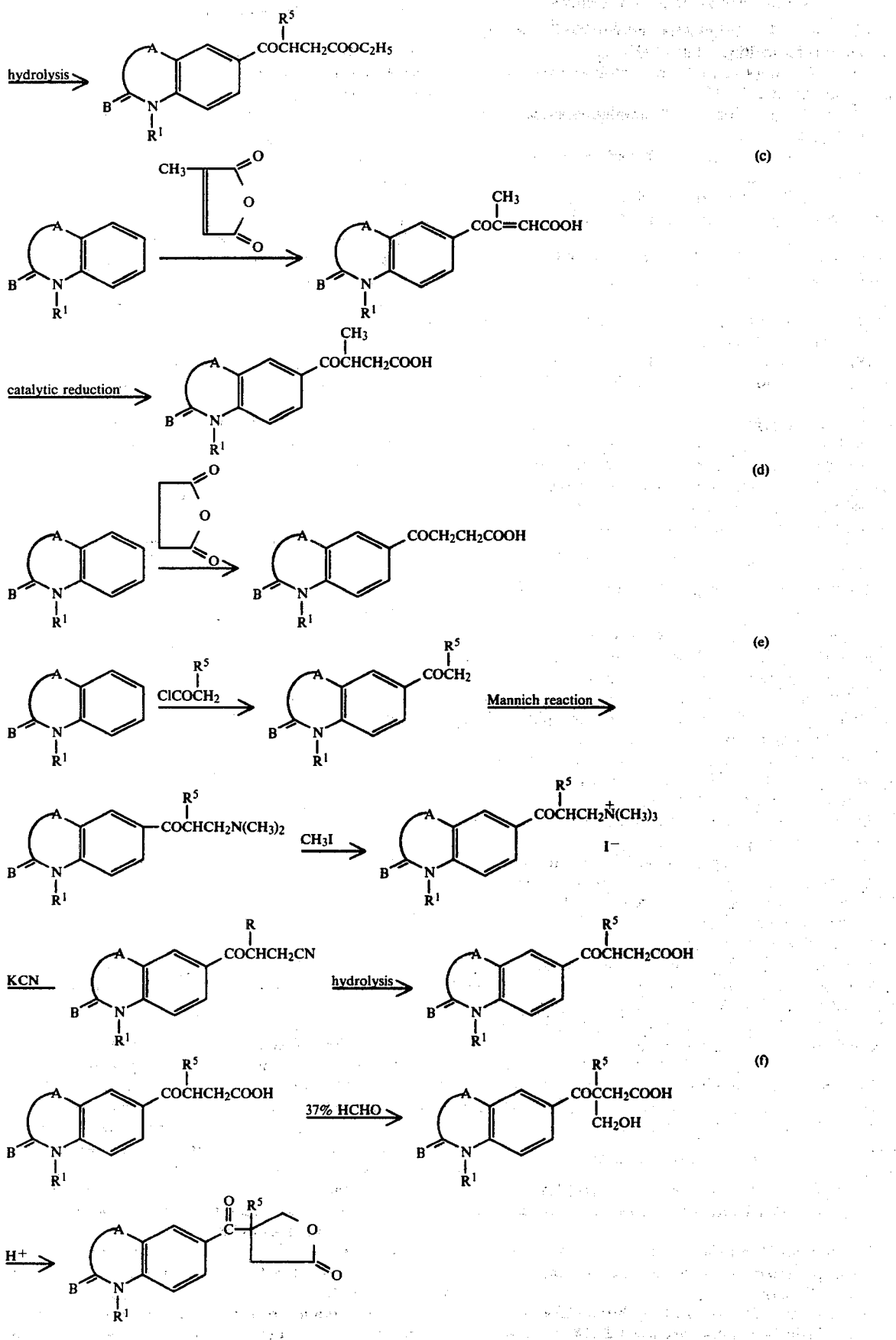

Examples of Starting Compounds (1) 4-Oxo-4-(1-methyl-2-oxoindolin-5-yl)-3-methylbutanoic acid, melting at 180°–182° C.;

(2) 4-Oxo-4-(1-methyl-2-oxoindolin-5-yl)butanoic acid, melting at 236°–240° C.;

(3) 4-Oxo-4-(indolin-5-yl)-3-methylbutanoic acid, melting at 193°–195° C.;

(4) 4-Oxo-4-(1,2,3,4-tetrahydroquinolin-6-yl)-3-methylbutanoic acid;

(5) 4-Oxo-4-(1,4,4-trimethyl-2-oxo-1,2,3,4-tetrahydroquinolin-6-yl)-3-methylbutanoic acid, melting at 133°–135° C.;

(6) 4-Oxo-4-(4-methyl-2-oxo-1,2,3,4-tetrahydroquinolin-6-yl)-3-methylbutanoic acid, melting at 172°–174° C.;

(7) 4-Oxo-4-(1,4,4-trimethyl-2-oxo-1,2,3,4-tetrahydroquinolin-6-yl)butanoic acid, melting at 194°–197° C.;

(8) 4-(1-Ethyl-2-oxo-1,2,3,4-tetrahydroquinolin-6-yl)carbonyl-Y-butyrolactone, melting at 135°–138° C.; and (9) 4-(1-Methyl-2-oxo-1,2,3,4-tetrahydroquinolin-6-yl)carbonyl-Y-butyrolactone, melting at 142°–144° C.

The compounds of formula (I) and pharmaceutically acceptable acid addition salts thereof have inhibitory activities on platelet aggregation and antihypertensive activities as shown, for example, by the following tests:

TESTING METHODS

I. Inhibitory activity on platelet aggregation in rats and rabbits

A group of 4–6 rats (250–300 g) or 3 rabbits (3–3.5 kg) was used. The citrated blood was obtained 2 hours after the oral treatment with test compounds. The platelet aggregation of platelet rich-plasma was induced by addition of $1.5 \times 10^{-5}$ M adenosine diphosphate (final concentration) and was measured with a Born type six channel aggregometer (G.V.R. Born, J. Physiol. 162, 67 (1962)). Results are shown in the following Table I as the percent inhibition of the aggregation as compared with the control group. II. Antihypertensive activity in spontaneously hypertensive rats A group of 5 spontaneously hypertensive rats (300–350 g) was used. Tail blood pressure was determined by a rat tail manometer (NARCO, PE-300) without anesthesia immediately before and 5 hours after the oral treatment with test compounds. The rat was warmed at 40° C. for 10 minutes. The apparatus detects blood flow pulses in the tail by a pulse sensor. The arterial blood flow was interrupted by applying pressure to the tail through a pneumatic cuff. The blood flow reappeared when the cuff pressure was decreased. The value was approximately equal to the maximum blood pressure. Results are shown in the following Table I as mmHg in a decrease of maximum blood pressure at 5 hours after the treatment.

TEST COMPOUNDS

Compound A: 6-(5-Methyl-3-oxo-2,3,4,5-tetrahydropyridazin-6-yl)-1-methyl-1,2,3,4-tetrahydroquinolin-2-one Compound B: 6-(5-Acetoxymethyl-3-oxo-2,3,4,5-tetrahydropyridazin-6-yl)-1-methyl-1,2,3,4-tetrahydroquinolin-2-one Compound C: 6-(5-Methyl-3-oxo-2,3,4,5-tetrahydropyridazin-6-yl)-1,4,4-trimethyl-1,2,3,4-tetrahydroquinolin-2-one Compound D: 6-(5-Methyl-3-oxo-2,3,4,5-tetrahydropyridazin-6-yl)-1,4-dimethyl-1,2,3,4-tetrahydroquinolin-2-one Compound E: 6-(5-Hydroxymethyl-3-oxo-2,3,4,5-tetrahydropyridazin-6-yl)-1,4,4-trimethyl-1,2,3,4-tetrahydroquinolin-2-one Compound F: 6-(5-Hydroxymethyl-3-oxo-2,3,4,5-tetrahydropyridazin-6-yl)-1-methyl-1,2,3,4-tetrahydroquinolin-2-one Compound G: 6-(5-Ethyl-3-oxo-2,3,4,5-tetrahydropyridazin-6-yl)-1-ethyl-1,2,3,4-tetrahydroquinolin-2-one Compound H: 6-(5-Hydroxymethyl-3-oxo-2,3,4,5-tetrahydropyridazin-6-yl)-1-ethyl-1,2,3,4-tetrahydroquinolin-2-one Compound I: 6-(5-Acetoxymethyl-3-oxo-2,3,4,5-tetrahydropyridazin-6-yl)-1-ethyl-1,2,3,4-tetrahydroquinolin-2-one Compound J: 6-(5-Methyl-3-oxo-2,3,4,5-tetrahydropyridazin-6-yl)-1-ethyl-1,2,3,4-tetrahydroquinolin-2-one Compound K: 6-[5-Methyl-2-(2-morpholinoethyl)-3-oxo-2,3,4,5-tetrahydropyridazin-6-yl]-1-methyl-1,2,3,4-tetrahydroquinolin-2-one hydrochloride hemihydrate

RESULTS

TABLE I

| Compound | Dose (mg/kg, po) | Percent inhibition of platelet aggregation | | Decrease of tail blood pressure (mmHg) in SHR |
|---|---|---|---|---|
| | | Rat | Rabbit | |
| A | 0.03 | 62 | 93 ± 2(SE) | |
| | 0.10 | 61 | | |
| | 0.30 | | | 23 |
| | 1.0 | | | 56 |
| B | 3 | 51 | 85 ± 6 | 31 |
| | 30 | | | 62 |
| C | 3 | 59 | 93 ± 1 | 48 |
| | 30 | | | 63 |
| D | 0.1 | 38 | | |
| | 0.3 | | 78 ± 6 | 16 |
| | 3.0 | | | 71 |
| E | 10 | 43 | | |
| | 30 | | 48 ± 16 | |
| F | 3 | 62 | | |
| | 30 | | | 92 |
| G | 3 | 34 | | |
| H | 3 | 46 | | |
| I | 3 | 46 | | |
| | 30 | | | 47 |
| J | 3 | 35 | | |
| K | 3 | 51 | 75 ± 8 | 45 |

The inhibitory agents of platelet aggregation are useful in the prophylaxis or therapy of platelet-induced thromboembolism, and in modifying other platelet-mediated phathologic processes such as atherosclerosis in human beings. Therefore, these agents are useful as the drugs for treatment of the patients with following diseases or disorders: (i) cerebrovascular disorders such as transient ischemic attacks, transient monocular blindness or completed stroke, (ii) ischemic heart diseases such as a myocardial infarction, (iii) thrombosis in other arteries, (iv) microcirculatory thrombosis and (v) venous thrombosis. These agents are also used for patients with prosthetic heart valves or arterio-venous shunts, and are useful as antihypertensive drugs.

The compounds of formula (I) and pharmaceutically acceptable acid addition salts thereof can be administered safely as antithrombotic or antihypertensive drugs, either alone or in the form of a pharmaceutical preparation with a suitable and conventional carrier or adjuvant, administered orally, without harmful side effects to the patients.

The pharmaceutical composition can take the form of tablets, granules, powder or capsules, for oral administration, of injectable solution for subcutaneous or intramuscular administration. The choice of carrier is determined by the preferred form of administration, the solubility of the compounds and standard pharmaceutical practice.

Formulation Example 10 mg tablets are prepared from the following compositions:

| | |
|---|---|
| Compound A | 10.0 mg |
| Lactose | 32.0 mg |
| Microcrystalline cellulose | 4.7 mg |
| Corn starch | 12.0 mg |
| Magnesium stearate | 0.3 mg |
| Talc | 1.0 mg |
| | 60.0 mg |

The oral daily dose of the compounds of formula (I) or pharmaceutically acceptable acid addition salts thereof for human adults usually ranges from 0.1 to 100 mg, but it may vary depending upon the age, body weight, and/or severity of the conditions to be treated as well as the responses to the medication.

The present invention is further explained by way of the following illustrative examples:

EXAMPLE 1

A solution of 7 g of 4-oxo-4-(1-methyl-2-oxoindolin-5-yl)butanoic acid and 3 ml of hydrazine hydrate in 70 ml of dimethylformamide was heated on a water bath for 4 hours. The precipitated crystals were filtered off and recrystallized from dimethylformamide to give 4.0 g of 5-(3-oxo-2,3,4,5-tetrahydropyridazin-6-yl)-1-methylindolin-2-one as pale yellow prisms, melting at 261°–264° C.

EXAMPLE 2

A solution of 27 g of 4-oxo-4-(indolin-5-yl)-3-methylbutanoic acid hydrochloride and 15 ml of hydrazine hydrate in 200 ml of ethanol was heated under reflux on a water bath for 2 hours. The reaction mixture was concentrated under reduced pressure and water was added to the residue. The precipitated crystals were filtered off, washed with water and recrystallized from ethanol to give 20 g of 5-(5-methyl-3-oxo-2,3,4,5-tetrahydropyridazin-6-yl)indoline as white crystals, melting at 187°–189° C.

EXAMPLE 3

To a solution of 5-(5-methyl-3-oxo-2,3,4,5-tetrahydropyridazin-6-yl)indoline in 100 ml of chloroform was added 5 ml of triethylamine with stirring. To the mixture was added dropwise 3 ml of acetic anhydride. After maintaining at room temperature for one hour, the reaction mixture was concentrated under reduced pressure. The residual crystals were filtered off, washed with water and recrystallized from ethanol to give 4.3 g of 5-(5-methyl-3-oxo-2,3,4,5-tetrahydropyridazin-6-yl)-1-acetylindoline as white crystals, melting at 258°–261° C.

The following compounds can be prepared in an analogous manner mentioned in the above Examples:
5-(3-Oxo-2,3,4,5-tetrahydropyridazin-6-yl)indolin-2-one, melting at 340° C. with decomposition;
5-(5-Methyl-3-oxo-2,3,4,5-tetrahydropyridazin-6-yl)indolin-2-one, melting at 276° C.;
5-(5-Methyl-3-oxo-2,3,4,5-tetrahydropyridazin-6-yl)-1-methylindolin-2-one, melting at 213°–214° C.;
5-(5-Methyl-3-oxo-2,3,4,5-tetrahydropyridazin-6-yl)-1-methanesulfonylindoline, melting at 230°–232° C.;
6-(3-Oxo-2,3,4,5-tetrahydropyridazin-6-yl)-1-acetyl-1,2,3,4-tetrahydroquinoline, melting at 210° C.;
6-(3-Oxo-2,3,4,5-tetrahydropyridazin-6-yl)-1,2,3,4-tetrahydroquinoline, melting at 166°–168° C.;
6-(3-Oxo-2,3,4,5-tetrahydropyridazin-6-yl)-1-(4-fluorobenzoyl)-1,2,3,4-tetrahydroquinoline,
6-(3-Oxo-2,3,4,5-tetrahydropyridazin-6-yl)-1-(3,4-dichlorobenzoyl)-1,2,3,4-tetrahydroquinoline;
6-(3-Oxo-2,3,4,5-tetrahydropyridazin-6-yl)-1-(4-methoxybenzoyl)-1,2,3,4-tetrahydroquinoline;
6-(5-Methyl-3-oxo-2,3,4,5-tetrahydropyridazin-6-yl)-1,2,3,4-tetrahydroquinoline, melting at 154°–157° C.;
6-(5-Methyl-3-oxo-2,3,4,5-tetrahydropyridazin-6-yl)-1-acetyl-1,2,3,4-tetrahydroquinoline, melting at 175°–178° C.;
6-(3-Oxo-2,3,4,5-tetrahydropyridazin-6-yl)-1-(4-methylbenzoyl)-1,2,3,4-tetrahydroquinoline;
5-(5-Butyl-3-oxo-2,3,4,5-tetrahydropyridazin-6-yl)indoline;
6-(5-Methyl-3-oxo-2,3,4,5-tetrahydropyridazin-6-yl)-1-methyl-1,2,3,4-tetrahydroquinolin-2-one, melting at 166°–168° C.;
6-(5-Methyl-3-oxo-2,3,4,5-tetrahydropyridazin-6-yl)-1,2,3,4-tetrahydroquinolin-2-one, melting at 300°–305° C. with decomposition;
6-(5-Methyl-3-oxo-2,3,4,5-tetrahydropyridazin-6-yl)-1-(4-chlorobenzoyl)-1,2,3,4-tetrahydroquinoline, melting at 236°–238° C.; and
6-(5-Methyl-3-oxo-2,3,4,5-tetrahydropyridazin-6-yl)-1-methyl-1,2,3,4-tetrahydroquinoline, melting at 164°–165° C.

EXAMPLE 4

A solution of 2.72 g of 4-oxo-4-(1-methyl-2-oxo-1,2,3,4-tetrahydroquinolin-6-yl)-3-methylbutanoic acid and 1.5 g of 2-hydrazinoethanol in 30 ml of ethanol was heated under reflux on a water bath for 2 hours. The reaction mixture was concentrated under reduced pressure and water was added to the residue. The precipitated crystals were filtered off and recrystallized from isopropanol to give 2.5 g of 6-[2-(2-hydroxyethyl)-5-methyl-3-oxo-2,3,4,5-tetrahydropyridazin-6-yl]-1-methyl-1,2,3,4-tetrahydroquinolin-2-one as colorless crystals, melting at 171°–173° C.

EXAMPLE 5

To a solution of 5.4 g of 6-(5-methyl-3-oxo-2,3,4,5-tetrahydropyridazin-6-yl)-1-methyl-1,2,3,4-tetrahydroquinolin-2-one in 50 ml of dimethylformamide was added 1.1 g of 50% sodium hydride. After stirring for about 30 minutes, 2.4 g of ethyl bromide was added and the mixture was stirred at about 40° C. for one hour. The reaction mixture was poured into 200 ml of water and extracted with 100 ml of ethyl acetate. The extract was dried over magnesium sulfate and concentrated under reduced pressure. The residue was recrystallized from ethanol to give 3.7 g of 6-(2-ethyl-5-methyl-3-oxo-2,3,4,5-tetrahydropyridazin-6-yl)-1-methyl-1,2,3,4-tetrahydroquinolin-2-one as colorless crystals, melting at 170°–172° C.

The following compounds can be prepared in an analogous manner mentioned in the above Examples:

6-[2-(2-Naphthyloxy)ethyl-5-methyl-3-oxo-2,3,4,5-tetrahydropyridazin-6-yl]-1-methyl-1,2,3,4-tetrahydroquinolin-2-one, melting at 127°–129° C.;

5-[2-(2-Hydroxyethyl)-5-methyl-3-oxo-2,3,4,5-tetrahydropyridazin-6-yl]-indoline, melting at 117°–120° C.;

6-(2-Butyl-5-methyl-3-oxo-2,3,4,5-tetrahydropyridazin-6-yl)-1-methyl-1,2,3,4-tetrahydroquinolin-2-one, melting at 109°–110° C.;

6-(5-Methyl-2-octadecyl-3-oxo-2,3,4,5-tetrahydropyridazin-6-yl)-1-methyl-1,2,3,4-tetrahydroquinolin-2-one, melting at 66°–70° C.;

6-(2-Docosyl-5-methyl-3-oxo-2,3,4,5-tetrahydropyridazin-6-yl)-1-methyl-1,2,3,4-tetrahydroquinolin-2-one, melting at 65°–67° C.;

6-(5-Methyl-2-pentadecyl-3-oxo-2,3,4,5-tetrahydropyridazin-6-yl)-1-methyl-1,2,3,4-tetrahydroquinolin-2-one, melting at 68.5°–70.5° C.;

6-[2-(4-Oxopentyl)-5-methyl-3-oxo-2,3,4,5-tetrahydropyridazin-6-yl]-1-methyl-1,2,3,4-tetrahydroquinolin-2-one, melting at 80°–83° C.;

6-[2-(10-Carbamoyldecyl)-5-methyl-3-oxo-2,3,4,5-tetrahydropyridazin-6-yl]-1-methyl-1,2,3,4-tetrahydroquinolin-2-one, melting at 77°–81° C.;

6-(2-Heptadecyl-5-methyl-3-oxo-2,3,4,5-tetrahydropyridazin-6-yl)-1-methyl-1,2,3,4-tetrahydroquinolin-2-one, melting at 76°–78° C.;

6-(2-Hexadecyl-5-methyl-3-oxo-2,3,4,5-tetrahydropyridazin-6-yl)-1-methyl-1,2,3,4-tetrahydroquinolin-2-one, melting at 70°–71° C.; and 5-(2-Methyl-3-oxo-2,3,4,5-tetrahydropyridazin-6-yl)-1-methylindolin-2-one, melting at 200°–203° C.

EXAMPLE 6

To a solution of 3 g of 6-(5-methyl-3-oxo-2,3,4,5-tetrahydropyridazin-6-yl)-1,4,4-trimethyl-1,2,3,4-tetrahydroquinolin-2-one in 30 ml of dimethylformamide was added 0.9 g of 50% sodium hydride. After stirring for about 30 minutes, 1.7 g of 2-morpholinoethyl chloride was added and the mixture was stirred at about 50° C. for one hour. The reaction mixture was poured into 200 ml of ice-cold water and extracted with 150 ml of chloroform. The extract was dried over potassium carbonate and concentrated under reduced pressure. To the residue was added alcoholic hydrogen chloride and the precipitated crystals were filtered off. Recrystallization from isopropanol gave 2.5 g of 6-[5-methyl-2-(2-morpholinoethyl)-3-oxo-2,3,4,5-tetrahydropyridazin-6-yl]-1,4,4-trimethyl-1,2,3,4-tetrahydroquinolin-2-one hydrochloride, melting at 243°–246° C.

The following compounds can be prepared in an analogous manner mentioned in the above Example:

6-[5-Methyl-2-(2-morpholinoethyl)-3-oxo-2,3,4,5-tetrahydropyridazin-6-yl]-1-methyl-1,2,3,4-tetrahydroquinolin-2-one hydrochloride hemihydrate, melting at 221°–229° C.;

6-[5-Methyl-2-(3-piperidinopropyl)-3-oxo-2,3,4,5-tetrahydropyridazin-6-yl]-1-methyl-1,2,3,4-tetrahydroquinolin-2-one hydrochloride, melting at 232°–233° C.;

6-[5-Methyl-2-(3-(4-methylpiperazin-1-yl)propyl)-3-oxo-2,3,4,5-tetrahydropyridazin-6-yl]-1-methyl-1,2,3,4-tetrahydroquinolin-2-one dihydrochloride, melting at 257°–259° C. with decomposition;

6-[2-(2-Dimethylaminoethyl)-5-methyl-3-oxo-2,3,4,5-tetrahydropyridazin-6-yl]-1-methyl-1,2,3,4-tetrahydroquinolin-2-one hydrochloride, melting at 237°–239° C. with decomposition; and 6-[2-(3-Dimethylaminopropyl)-5-methyl-3-oxo-2,3,4,5-tetrahydropyridazin-6-yl]-1,4,4-trimethyl-1,2,3,4-tetrahydroquinolin-2-one hydrochloride hydrate, melting at 220°–224° C.

EXAMPLE 7

A mixture of 20 g of 4-oxo-4-(1,4,4-trimethyl-2-oxo-1,2,3,4-tetrahydroquinolin-6-yl)-3-methylbutanoic acid, 10 g of hydrazine hydrate and 200 ml of ethanol was heated under reflux for one hour. After cooling, the precipitated crystals were filtered off and recrystallized from ethanol to give 15.1 g of 6-(5-methyl-3-oxo-2,3,4,5-tetrahydropyridazin-6-yl)-1,4,4-trimethyl-1,2,3,4-tetrahydroquinolin-2-one, melting at 238°–241° C.

EXAMPLE 8

To a mixture of 6 g of 6-(5-methyl-3-oxo-2,3,4,5-tetrahydropyridazin-6-yl)-1,4,4-trimethyl-1,2,3,4-tetrahydroquinolin-2-one and 60 ml of dimethylformamide was added 1.8 g of sodium hydride. After 30 minutes, 4.6 g of butyl bromide was added to the mixture and the whole mixture was stirred for one hour. After completion of the reaction, the mixture was poured into ice-cold water and the precipitated crystals were filtered off and recrystallized from a mixture of ethanol and water to give 5.2 g of 6-(2-butyl-5-methyl-3-oxo-2,3,4,5-tetrahydropyridazin-6-yl)-1,4,4-trimethyl-1,2,3,4-tetrahydroquinolin-2-one, melting at 137°–139° C.

EXAMPLE 9

To a mixture of 12 g of 6-(5-methyl-3-oxo-2,3,4,5-tretrahydropyridazin-6-yl)-4-methyl-1,2,3,4-tetrahydroquinolin-2-one and 200 ml of acetic acid was added dropwise 8.4 g of bromine. The mixture was heated with stirring at 60°–70° C. for 3 hours and then the solvent was distilled off under reduced pressure. To the residue was added water and the precipitated crystals were filtered off. Recrystallization from acetic acid gave 6.5 g of 6-(5-methyl-3-oxo-2,3-dihydropyridazin-6-yl)-4-methyl-1,2,3,4-tetrahydroquinolin-2-one, melting at above 300° C.

EXAMPLE 10

A mixture of 5.4 g of 6-(5-methyl-3-oxo-2,3,4,5-tetrahydropyridazin-6-yl)-1-methyl-1,2,3,4-tetrahydroquinolin-2-one, 5.5 g of 2,3-dichloro-5,6-dicyano-1,4-benzoquinone and 500 ml of benzene was heated under reflux for 48 hours. After cooling, the precipitated crystals were filtered off. The filtrate was washed with a 10% sodium hydroxide solution and dried over sodium sulfate. The solvent was distilled off under reduced pressure. The residue and the crystals were combined and purified by using a column chromatograph. The resulting crystals were recrystallized from methanol to give 1.5 g of 6-(5-methyl-3-oxo-2,3,4,5-tetrahydropyridazin-6-yl)-1-methyl-1,2-dihydroquinolin-2-one, melting at 248°–251° C.

The following compounds can be prepared in an analogous manner mentioned in the above Examples:

6-(5-Methyl-3-oxo-2,3,4,5-tetrahydropyridazin-6-yl)-1,4-dimethyl-1,2,3,4-tetrahydroquinolin-2-one, melting at 223°–225° C.;

6-(5-Methyl-3-oxo-2,3,4,5-tetrahydropyridazin-6-yl)-4-methyl-1,2,3,4-tetrahydroquinolin-2-one, melting at 275°-178° C.;

6-(3-Oxo-2,3,4,5-tetrahydropyridazin-6-yl)-1,4,4-trimethyl-1,2,3,4-tetrahydroquinolin-2-one, melting at 233°-235° C.;

6-(2,5-Dimethyl-3-oxo-2,3,4,5-tetrahydropyridazin-6-yl)-1,4,4-trimethyl-1,2,3,4-tetrahydroquinolin-2-one, melting at 165°-169° C.;

6-(5-Methyl-3-oxo-2,3-dihydropyridazin-6-yl)-1,4,4-trimethyl-1,2,3,4-tetrahydroquinolin-2-one, melting at 270°-274° C.;

6-(5-Methyl-3-oxo-2,3,4,5-tetrahydropyridazin-6-yl)-1,4-dimethyl-1,2-dihydroquinolin-2-one;

6-(5-Methyl-3-oxo-2,3-dihydropyridazin-6-yl)-1-methyl-1,2-dihydroquinolin-2-one;

6-(5-Methyl-3-oxo-2,3,4,5-tetrahydropyridazin-6-yl)-1-ethyl-4-methyl-1,2,3,4-tetrahydroquinolin-2-one;

6-(5-Ethyl-3-oxo-2,3,4,5-tetrahydropyridazin-6-yl)-1,4,4-trimethyl-1,2,3,4-tetrahydroquinolin-2-one;

6-(2-Ethyl-5-methyl-3-oxo-2,3,4,5-tetrahydropyridazin-6-yl)-1,4,4-trimethyl-1,2,3,4-tetrahydroquinolin-2-one;

6-(5-Ethyl-3-oxo-2,3,4,5-tetrahydropyridazin-6-yl)-1,4-dimethyl-1,2-dihydroquinolin-2-one;

6-(5-Methyl-2-propyl-3-oxo-2,3,4,5-tetrahydropyridazin-6-yl)-1,4-dimethyl-1,2-dihydroquinolin-2-one;

6-(2,5-Dimethyl-3-one-2,3-dihydropyrdazin-6-yl)-1,4-dimethyl-1,2-dihydroquinolin-2-one; and 6-(5-Methyl-3-oxo-2,3,4,5-tetrahydropyridazin-6-yl)-1-butyl-4,4-dimethyl-1,2,3,4-tetrahydroquinolin-2-one.

EXAMPLE 11

A solution of 4.9 g of 4-(1-methyl-2-oxo-1,2,3,4-tetrahydroquinolin-6-yl)carbonyl-γ-butyrolactone and 3.0 ml of 85% hydrazine hydrate in 50 ml of ethanol was heated under reflux overnight. The reaction mixture was concentrated under reduced pressure and ice-cold water was added to the residue. After the mixture was allowed to stand, the precipitated crystals were filtered off and recrystallized from water to give 2.5 g of 6-(5-hydroxymethyl-3-oxo-2,3,4,5-tetrahydropyridazin-6-yl)-1-methyl-1,2,4,5-tetrahydroquinolin-2-one as colorless prisms, melting at 201°-204° C.

EXAMPLE 12

A solution of 13.6 g of 6-(5-hydroxymethyl-3-oxo-2,3,4,5-tetrahydropyridazin-6-yl)-1-methyl-1,2,3,4-tetrahydroquinolin-2-one, 5.8 g of acetic anhydride and 10 ml of triethylamine in 300 ml of chloroform was heated under reflux on a water bath for 3 hours. The reaction mixture was washed with water, dried over potassium carbonate and concentrated under reduced pressure. The residue was dissolved into a small amount of ethyl acetate. After the solution was allowed to stand, the precipitated crystals were filtered off and recrystallized from isopropanol to give 7.3 g of 6-(5-acetoxymethyl-3-oxo-2,3,4,5-tetrahydropyridazin-6-yl)-1-methyl-1,2,3,4-tetrahydroquinolin-2-one as needles, melting at 149°-153° C.

The following compounds can be prepared in an analogous manner mentioned in the above Examples:

6-(5-Hydroxymethyl-3-oxo-2,3,4,5-tetrahydropyridazin-6-yl)-1,2,3,4-tetrahydroquinolin-2-one, melting at 325°-330° C.;

6-(5-Hydroxymethyl-3-oxo-2,3,4,5-tetrahydropyridazin-6-yl)-1,4,4-trimethyl-1,2,3,4-tetrahydroquinolin-2-one, melting at 241°-243° C.;

6-(5-Hydroxymethyl-3-oxo-2,3,4,5-tetrahydropyridazin-6-yl)-1-ethyl-1,2,3,4-tetrahydroquinolin-2-one, melting at 198°-200° C.;

6-(5-Acetoxymethyl-3-oxo-2,3,4,5-tetrahydropyridazin-6-yl)-1-ethyl-1,2,3,4-tetrahydroquinolin-2-one, melting at 157°-159° C.;

6-(5-Hydroxymethyl-5-methyl-3-oxo-2,3,4,5-tetrahydropyridazin-6-yl)-1-methyl-1,2,3,4-tetrahydroquinolin-2-one, melting at 218°-219° C.;

6-(5-Acetoxymethyl-3-oxo-2,3,4,5-tetrahydropyridazin-6-yl)-1-methyl-1,2,3,4-tetrahydroquinolin-2-one, melting at 230°-232° C.;

6-(5-Butyryloxymethyl-3-oxo-2,3,4,5-tetrahydropyridazin-6-yl)-1-methyl-1,2,3,4-tetrahydroquinolin-2-one, melting at 93°-98° C.;

6-(5-Hydroxymethyl-2-methyl-3-oxo-2,3,4,5-tetrahydropyridazin-6-yl)-1-methyl-1,2,3,4-tetrahydroquinolin-2-one;

6-(5-Hydroxymethyl-3-oxo-2,3,4,5-tetrahydropyridazin-6-yl)-1,4-dimethyl-1,2-dihydroquinolin-2-one;

6-(5-Hydroxymethyl-3-oxo-2,3,4,5-tetrahydropyridazin-6-yl)-1,4-dimethyl-1,2,3,4-tetrahydroquinolin-2-one, melting at 222°-223° C.;

6-(2-Butyl-5-hydroxymethyl-3-oxo-2,3,4,5-tetrahydropyridazin-6-yl)-1-methyl-1,2,3,4-tetrahydroquinolin-2-one; and 6-(5-Acetoxymethyl-3-oxo-2,3,4,5-tetrahydropyridazin-6-yl)-1,4-dimethyl-1,2,3,4-tetrahydroquinolin-2-one.

What is claimed is:

1. A pyridazinone compound of the formula:

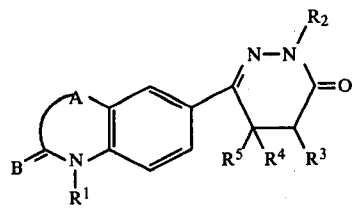

and a pharmaceutically acceptable acid addition salt thereof, wherein A is methylene, ethylene, $C_{1-4}$ alkyl substituted ethylene, vinylene or $C_{1-4}$ alkyl substituted vinylene; B=C< is O=C< or $H_2$C<; $R^1$ is hydrogen, $C_{1-4}$ alkyl, $C_{2-4}$ alkanoyl, $C_{1-2}$ alkylsulfonyl, or mono- or di-substituted benzoyl each substituent being independently selected from the class consisting of halogen, $C_{1-4}$ alkyl or $C_{1-4}$ alkoxy; $R^2$ is hydrogen, alkyl, hydroxy $C_{1-4}$ alkyl, $C_{1-11}$ carbamoylalkyl, $C_{1-2}$ naphthyloxyalkyl, $C_{1-5}$ oxoalkyl or $(R^6)(R^7)N$—$(CH_2)_n$—, where each of $R^6$ and $R^7$ is hydrogen or $C_{1-4}$ alkyl, or $R^6$ alkyl, or $R^6$ and $R^7$ together with the adjacent nitrogen atom form pyrrolidine, piperidine, morpholine, piperazine or N-methylpiperazine and n is 2 or 3; $R^3$ is hydrogen; $R^4$ is hydrogen, $C_{1-4}$ alkyl, hydroxymethyl or $C_{2-4}$ alkanoyloxymethyl; and $R^5$ is hydrogen or $C_{1-4}$ alkyl; or $R^3$ and one of $R^4$ and $R^5$ together form a single bond.

2. The compound of claim 1 wherein A is ethylene, $C_{1-4}$ alkyl substituted ethylene, vinylene or $C_{1-4}$ alkyl substituted vinylene; B=C< is O+C<; $R^1$ is hydrogen or $C_{1-4}$ alkyl; $R^2$ is hydrogen, alkyl or $(R^6)(R^7)N$—$(CH_2)_n$—, where each of $R^6$ and $R^7$ is hydrogen or $C_{1-4}$ alkyl, or $R^6$ and $R^7$ together with the adjacent nitrogen atom form pyrrolidine, piperidine, morpholine, piperazine or N-methylpiperazine and n is 2 or 3; $R^{7\ 3}$ is hydrogen; $R^4$ is hydrogen, $C_{1-4}$ alkyl, hydroxymethyl or $C_{2-4}$ alkanoyloxymethyl; and $R^5$ is hydrogen or $C_{1-4}$ alkyl.

3. The compound of claim 1 wherein A is ethylene or $C_{1-4}$ alkyl substituted ethylene; $B=C<$ is $O+C<$; $R^1$ is hydrogen or $C_{1-4}$ alkyl; $R^2$ is hydrogen, $C_{1-4}$ alkyl or $(R^6)(R^7)N-(CH_2)_n-$, where each of $R^6$ and $R^7$ is hydrogen or $C_{1-4}$ alkyl, or $R^6$ and $R^7$ together with the adjacent nitrogen atom form pyrrolidine, piperidine, morpholine, piperazine or N-methylpiperazine and n is 2 or 3; $R^3$ is hydrogen; $R^4$ is hydrogen, $C_{1-4}$ alkyl, hydroxymethyl or $C_{2-4}$ alkanoyloxymethyl; and $R^5$ is hydrogen.

4. The compound of claim 1:
6-(5-Methyl-3-oxo-2,3,4,5-tetrahydropyridazin-6-yl)-1-methyl-1,2,3,4-tetrahydroquinolin-2-one 5. The compound of claim 1:
6-(5-Methyl-3-oxo-2,3,4,5-tetrahydropyridazin-6-yl)-1,4-dimethyl-1,2,3,4-tetrahydroquinolin-2-one 6. The compound of claim 1:
6-(5-Methyl-3-oxo-2,3,4,5-tetrahydropyridazin-6-yl)-1,4,4-trimethyl-1,2,3,4-tetrahydroquinolin-2-one 7. The compound of claim 1:
6-(5-Acetoxymethyl-3-oxo-2,3,4,5-tetrahydropyridazin-6-yl)-1-methyl-1,2,3,4-tetrahydroquinolin-2-one 8. The compound of claim 1:
6-(5-Hydroxymethyl-3-oxo-2,3,4,5-tetrahydropyridazin-6-yl)-1-methyl-1,2,3,4-tetrahydroquinoline-2-one 9. The compound of claim 1:
6-[5-Methyl-2-(2-morpholinoethyl)-3-oxo-2,3,4,5-tetrahydropyridazin-6-yl]-1-methyl-1,2,3,4-tetrahydroquinolin-2-one 10. The compound of claim 1:
6-(5-Ethyl-3-oxo-2,3,4,5-tetrahydropyridazin-6-yl)-1-ethyl-1,2,3,4-tetrahydroquinolin-2-one 11. The compound of claim 1:
6-(5-Hydroxymethyl-3-oxo-2,3,4,5-tetrahydropyridazin-6-yl)-1-ethyl-1,2,3,4-tetrahydroquinolin-2-one 12. The compound of claim 1:
6-(5-Acetoxymethyl-3-oxo-2,3,4,5-tetrahydropyridazin-6-yl)-1-ethyl-1,2,3,4-tetrahydroquinolin-2-one 13. The compound of claim 1:
6-(5-Methyl-3-oxo-2,3,4,5-tetrahydropyridazin-6-yl)-1-ethyl-1,2,3,4-tetrahydroquinolin-2-one 14. The compound of claim 1:
6-(5-Hydroxymethyl-3-oxo-2,3,4,5-tetrahydropyridazin-6-yl)-1,4,4-trimethyl-1,2,3,4-tetrahydroquinolin-2-one 15. The compound of claim 1:
6-(2,5-Dimethyl-3-oxo-2,3,4,5-tetrahydropyridazin-6-yl)-1,4,4-trimethyl-1,2,3,4-tetrahydroquinolin-2-one

* * * * *